United States Patent [19]

Freedman et al.

[11] Patent Number: 4,727,040
[45] Date of Patent: Feb. 23, 1988

[54] SPARGER FOR FERMENTATION AND TISSUE CULTURING VESSELS

[75] Inventors: David Freedman; Zheng Zhenbin, both of Highland Park, N.J.; Shaul Reuveny, Kfar, Israel

[73] Assignee: New Brunswick Scientific Co., Ltd., Edison, N.J.

[21] Appl. No.: 831,399

[22] Filed: Feb. 19, 1986

Related U.S. Application Data

[63] Continuation-in-part of Ser. No. 707,302, Mar. 1, 1985, abandoned.

[51] Int. Cl.⁴ ............................................. C12M 1/06
[52] U.S. Cl. .................... 435/315; 362/286; 362/313; 362/316; 362/287
[58] Field of Search ...................... 435/284–286, 435/313, 818, 813, 316, 314, 312, 287; 261/87; 417/108, 117

[56] References Cited

U.S. PATENT DOCUMENTS

| | | | |
|---|---|---|---|
| 2,641,455 | 6/1953 | Poirot | 261/87 X |
| 2,716,509 | 8/1955 | Saul | 417/108 X |
| 2,786,026 | 3/1957 | Stark | 417/108 X |
| 3,400,051 | 9/1968 | Hofschneider | 261/87 X |
| 3,603,509 | 9/1971 | Nechine | 261/122 X |
| 3,606,985 | 9/1971 | Reed | 261/124 |
| 3,957,585 | 5/1976 | Malick | 435/813 X |
| 4,079,008 | 3/1978 | Neumann | 261/124 X |
| 4,263,143 | 4/1981 | Ebner et al. | 261/87 X |
| 4,634,675 | 1/1987 | Freedman et al. | 435/284 X |
| 4,649,118 | 3/1987 | Anderson | 435/284 X |
| 4,656,138 | 4/1987 | Redikultsev et al. | 435/314 |

Primary Examiner—Larry Jones
Attorney, Agent, or Firm—Blum Kaplan

[57] ABSTRACT

A sparger for use in microcarrier fermentation systems is provided which includes a narrow, vertically extending outer chamber defined by a solid wall and a wall formed by a screen, wherein air or other gas is forced under pressure through a tube to the bottom of the chamber and from there to a distribution member for the release of the gas upwardly into the chamber. The top of the chamber is provided with exit openings which communicate to a point above the surface of the medium. In an alternate embodiment, gas is released at the bottom of an inner chamber defined by a wall formed with a plurality of screened windows.

25 Claims, 10 Drawing Figures

U.S. Patent  Feb. 23, 1988  Sheet 2 of 5  4,727,040
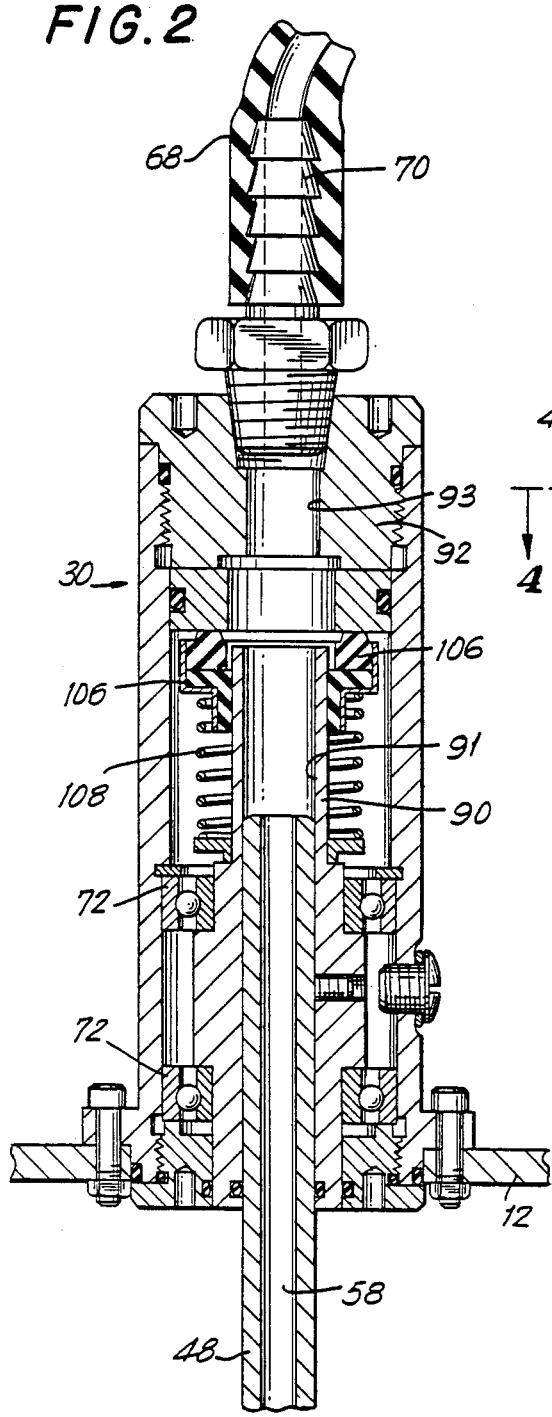
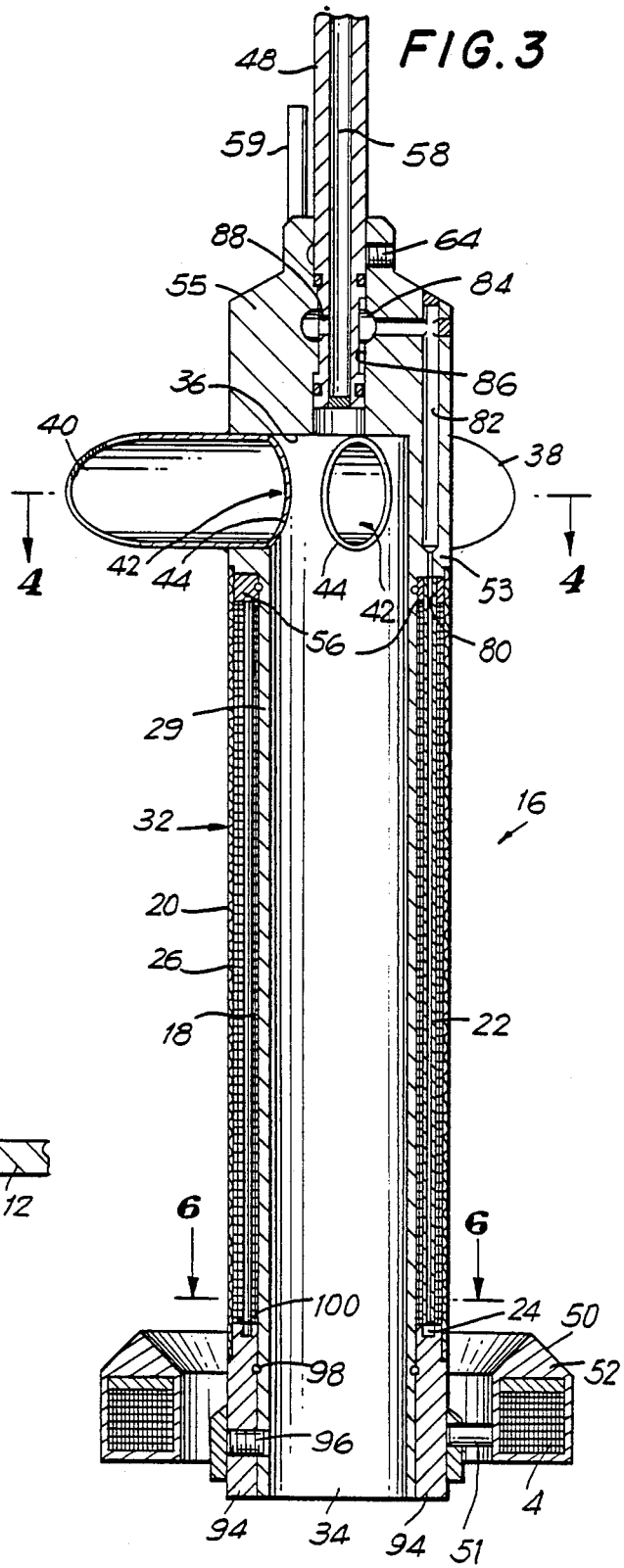

SPARGER FOR FERMENTATION AND TISSUE CULTURING VESSELS

This is a continuation-in-part of U.S. application Ser. No. 707,302 filed Mar. 1, 1985, now abandoned.

BACKGROUND OF THE INVENTION

This invention relates to a sparger for use in fermentation and tissue culturing vessels and in particular, to a sparger for use in microcarrier fermentation systems.

The use of cell culturing techniques are widely known, and are vital to the study of animal cell structure and for the production of important medical material such as hormones, enzymes, antibodies, vaccines, etc. When using tissue and microcarrier cell culturing techniques, the cells are ultra-fragile in nature, and easily damaged during growth. The culturing of anchorage-dependent cells has proved particularly difficult and the use of micorcarriers for this purpose has been developed. In microcarrier cultures, cells are grown as single layers and sometimes multilayers on a surface of microcarriers, generally small spheres, which are in turn suspended in a culture medium by gentle agitation. A detailed description of microcarrier cell culture principles may be found in the book "Microcarriers Cell Culture: Principles and Methods", Pharmacia Fine Chemicals, Sweden, December 1981.

It is important to provide air to microcarrier fermentation systems so as to provide oxygen to the cells. Additionally, it is also important to provide other gases to the system. A major problem, however, is that aeration is generally achieved by conventional means such as bubbling the gases through the fluid by placing a delivery tube in the fluid with an exit near the bottom thereof. This bubbling creates a form which is troublesome to most fermentation processes and can be fatal in microcarrier tissue culture processes.

A process has been developed to diffuse the air or other gases through a silicone rubber tube. However, the tube must have a large surface area and consequently, insufficient oxygen is transmitted to the medium.

It has also been proposed to deliver sparged air using a conventional tube to a point at the bottom of a cylindrical screen. The bubbles pass through the liquid within the screen which keeps the microcarriers away from the bubbles, thereby reducing the deleterious effects of foaming. This arrangement, however, has not proved satisfactory.

Accordingly, it is desirable to provide an improved sparger for use in microcarrier fermentation systems.

SUMMARY OF THE INVENTION

Generally speaking, in accordance with the invention, a sparger for use in microcarrier fermentation systems is provided. The sparger includes a chamber positioned in a liquid, the chamber being defined by at least a first wall formed in part by a screen. Gas is directed to the bottom of the chamber in order to aerate the liquid. A portion of the aerated liquid will pass through the screen but in fine bubbles so as to inhibit foaming in the liquid of the system.

In a first embodiment, the sparger of the invention includes a narrow, essentially vertically extending outer chamber defined by a solid wall and a wall formed from a screen. Air or other gas is then forced under pressure through at least one tube to the bottom of the outer chamber and from there to a distribution member having apertures distributed along the lower region of the outer chamber for the release of the gas upwardly into the chamber. The top of the outer chamber is provided with exit openings which communicate to a point above the surface of the medium. The gas bubbles through the column of fluid in the outer chamber, a portion of the gas passing through the screen in such fine bubbles so as to not cause foaming.

Gas distribution is enhanced by the distribution of the gas-rich nutrient by an agitator. An inner chamber defined by the solid wall has an open bottom end and a closed top end and includes at least one tubulation coupled to an opening in the solid wall in a region spaced from the open end thereof. The outer end of the tubulation defines an exit opening positioned so that the solid cylindrical wall is rotated about its axis, creating a suction force at the opening of the cylinder.

In an alternative embodiment, the sparger of the invention includes an outer solid wall and an inner wall defining a vertically extending outer chamber. The outer chamber has an open bottom end and a closed top end and includes at least one tubulation coupled to an opening in the solid wall, as described above. The inner wall has a plurality of windows covered by a screen and defines an inner chamber. A gas is forced under pressure to the bottom of the inner chamber and from there to a distribution member having apertures for releasing the gas into the chamber. The gas bubbles through the fluid in the inner chamber, the gas passing through the screens that cover the windows in such fine bubbles so as to not cause foaming.

Accordingly, it is an object of the invention to provide an improved sparger for fermentation systems and in particular, for microcarriers.

Yet another object of the invention is to provide an improved sparger for fermentation systems and in particular, microcarrier systems, which greatly enhances distribution of gases throughout the nutrient.

It is still a further object of the invention to provide an improved sparger for fermentation systems, and in particular, microcarrier systems, which minimize foaming.

It is still another object of the invention to provide an improved sparger for microcarrier fermentation systems which promotes improved cell culture growth.

It is still another object of the invention to provide an improved sparger for microcarrier fermentation systems which has scale up ability for use with various size vessels.

Still other objects and advantages of the invention will in part be obvious and will in part be apparent from the specification.

The invention accordingly comprises the features of construction, combinations of elements and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 2 is an enlarged, fragmentary cross-sectional view taken along line 2—2 of FIG. 1;

FIG. 3 is an enlarged, fragmentary cross-sectional view taken along line 3—3 of FIG. 2;

DETAILED DESCRIPTION OF THE DRAWINGS

Figure 1:
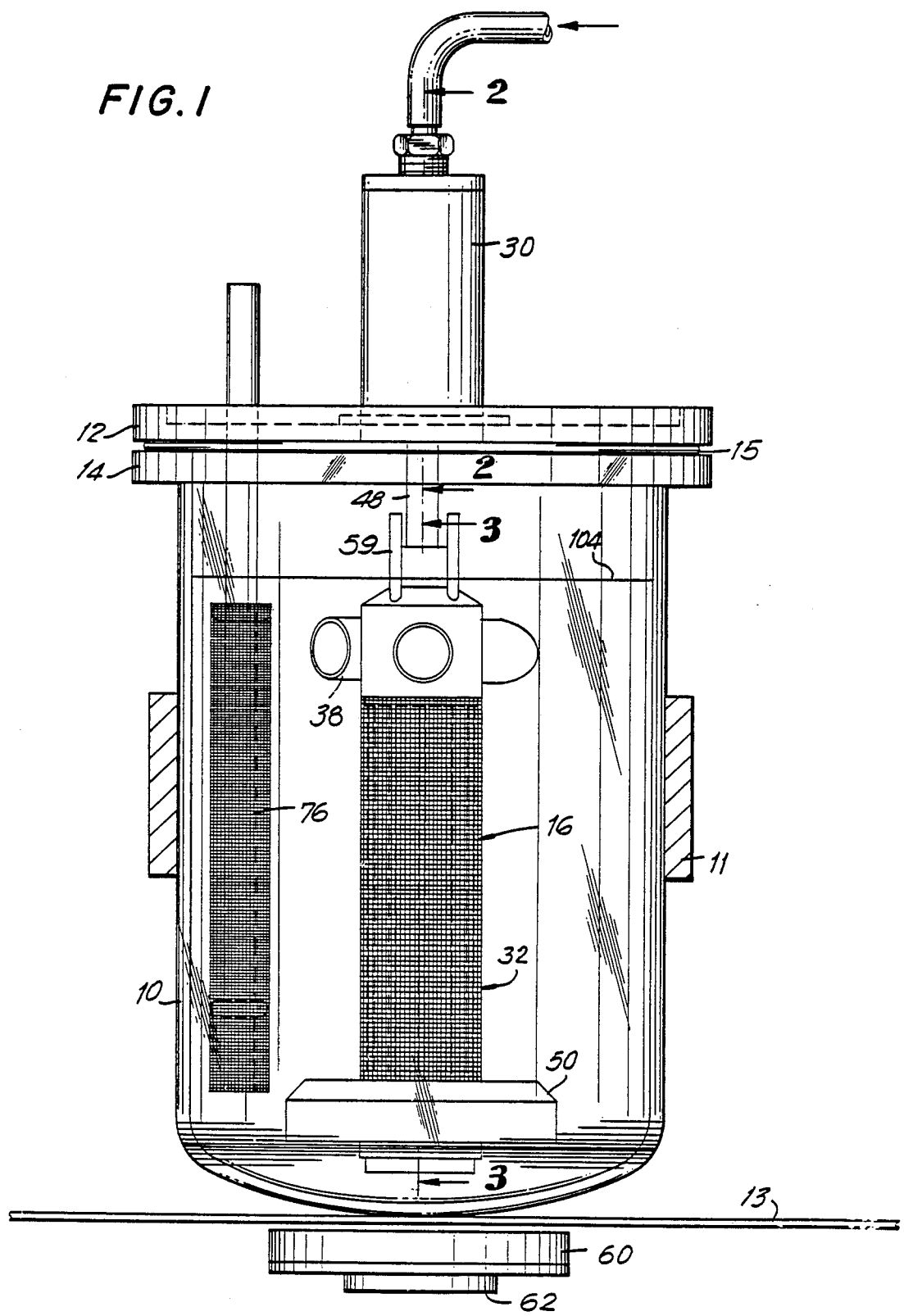
FIG. 1 is a plan view of an agitator using a sparger made according to the invention.

Reference is first made to FIG. 1, which illustrates a fermentation vessel 10, containing an agitator 16 therein. Vessel 10 is supported by a bracket 11 on a surface 13 of a controller (not shown) which may include the apparatus necessary to operate the fermentor. Vessel 10 is closed by means of vessel cap 12 which is sealed against the top rim 14 of vessel 10 through gasket 15. Agitator 16 is supported on vessel cap 12 and includes a cylindrical body assembly 32, as better illustrated in FIG. 3. Assembly 32 has a first open end 34 and a second closed end 36. The assembly includes three tubulations 38 which project laterally from assembly 32 aproximate to second closed end 36. Three tubulations 38 are positioned adjacent said closed end 36. Tubulations 38 are hollow, and include a first end defining an exit opening 40 and a second end 42. Second end 42 of each tubulation 38 is attached to body assembly 32 at an opening 44 in the inner cylindrical wall 29 thereof in order to permit fluid flow through open end 34, through openings 44 of the assembly and out exit openings 40.

Figure 4:
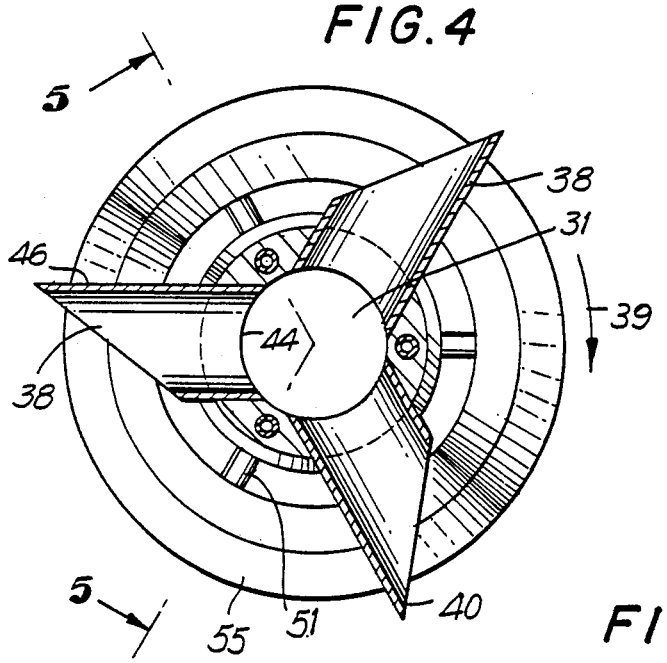
FIG. 4 is a cross-sectional view taken along line 4—4 of FIG. 3.

As illustrated in FIG. 4, exit openings 40 of each tubulation 38 are constructed so as to face in a direction opposite the direction of rotation (arrow 39) of agitator 16. During operation, body assembly 32 of agitator 16 is rotated about its longitudinal axis such that closed faces 46 of each tubulation 38 lead the movement of said tubulations. Consequently, a suction effect is created within assembly 32 and tubulations 38. This in turn causes the fluid within vessel 10 to flow into open end 34 of inner cylindrical wall 29, through the central core 31 of wall 29, into and through tubulations 38 and out of openings 40 of tubulations 38.

Figure 6:
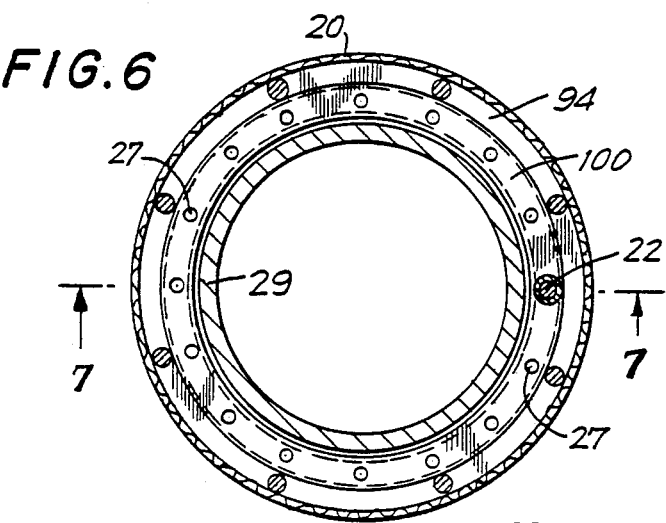
FIG. 6 is an enlarged, cross-sectional view taken along line 6—6 of FIG. 3.
Figure 7:
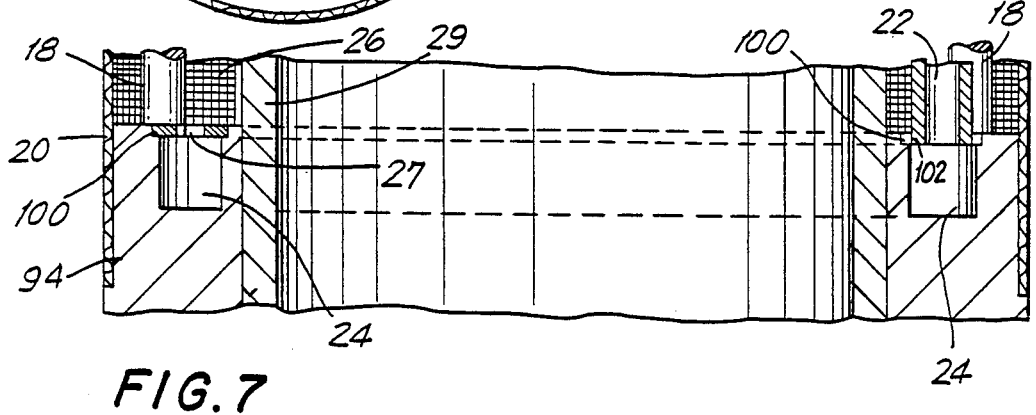
FIG. 7 is an enlarged, fragmentary cross-sectional view taken along line 7—7 of FIG. 6.

Referring to FIGS. 3, 6 and 7, agitator 16 contains an annular cylindrical chamber 26 defined by inner wall 29 of assembly 32 and an outer cylindrical screen 20. The upper portion of inner wall 29 terminates at a thickened region 53 which in turn is formed integrally with an end member 55 and defined end wall 36. Screen 20 is supported at its top by an annular member 56 which abuts against thickened region 53 and is provided with an internal O-ring 57 in engagement against the top of inner wall 29. A tube 22 extends longitudinally within chamber 26. Tube 22 is connected at its top to bore 80 extending through annular member 56 and is coupled to a gas input path including bore 82 through end member 55, an annular chamber 84 defined between the periphery of hollow shaft 48 and the bore 86 in end member 55 through which shaft 48 is journalled, lateral passage 88 in the wall of shaft 48, the central bore 58 in shaft 48, the bore 91 in moving shaft support member 90 (FIG. 2), the bore 93 in fixed shaft support member 92, gas supply nozzle 70 and gas supply tube 68 coupled thereto. Air or other gas is forced under pressure through the gas input path into tube 22.

As more particularly shown in FIGS. 3, 6 and 7, the bottom of screen 20 is supported on a cylindrical support member 94 coupled to the lower region of inner wall 29 by screws 96 and O-ring 98. The upper surface of support member 94 is formed with an annular cut-out defining, together with annular cap 100, an annular gas channel 24. Tube 22 communicates with channel 24 through an opening 102 in cap 100 (FIG. 7).

Annular cap 100 has apertures 27 extending along its upper surface for releasing gas upwardly into chamber 26. At this moment, chamber 26, along with vessel 10, contains a fluid medium. Gas released from apertures 27 bubbles through the column of fluid within chamber 26, some of the gas passing through screen 20 but in such fine bubbles so as to not cause any foaming. Additionally, some of the fluid within chamber 26, which has become heavily aerated due to the release of the gas, is forced out through screen 20.

Figure 5:
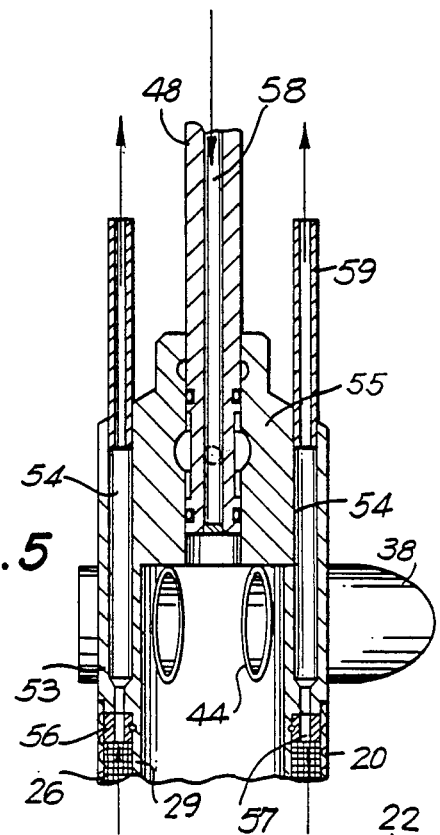
FIG. 5 is a cross-sectional view taken along line 5—5 of FIG. 4.

Annular member 56 is also formed with two exit tubes 59 connected respectively to two vertical exit bores 54 formed in end member 55 (FIG. 5). Exit tubes 59 are positioned in bores 55 and extend the level 104 of the fluid in the vessel 10. Fluid within chamber 26 is carried by the bubbles into bores 54 and out tubes 59, enhancing the distribution of gas throughout the fluid. This distribution is further enhanced by the operation of agitator 16 as previously described.

Agitator 16 is mounted on shaft 48 by means of a set screw 64. Shaft 48 in turn is rotably supported by a bearing assembly 30, as shown in FIG. 2. Bearing assembly 30 includes bearings 72 which allows rotation of shaft 48 and in turn agitator 16 when a rotational force is applied. Gaskets 106, maintained in contact by spring 108, prevent liquid escape while also promoting rotation of shaft 48. The fixed portion of bearing assembly 30 is coupled to cover 12 of vessel 10.

Attention is directed to FIGS. 1 and 3 which show an annular magnetic assembly affixed to cylindrical support member 94 by rods 51. Magentic assembly 50 includes an annular permanent magnet 4 surrounded and supported by a protective sheath 52. When magnet 60 of the magnetic drive motor 62 mounted below support 13 rotates, it causes the magnetic assembly 50 to rotate as well, thereby turning agitator 16 and shaft 48 on the axis defined by said shaft. When utilizing this method, no direct physical connection between the drive motor and the agitator is required. Further, magnetic assembly 50 aids in spreading the flow path on the bottom of vessel 10 and in preventing accumulation of microcarriers at the periphery of the bottom. This device may be also mechanically driven from above or below by direct drive motor means so that the agitator 16 is rotated without the use of magnets.

In a preferred construction, screen 20 of the sparger may be supported by the cage of rods 18 which extend between annular member 56 and support member 94. The cage of rods 18, annular member 56, and support member 94, together with tube 22 and screen 20 can be removed as a unit. Fluid delivery could extend through the upper annular ring. The bottom annular ring could be formed with an annular groove covered by an annular disk having apertures therein and through which the delivery tube extends. Such an arrangement corresponds functionally to the above-mentioned ring-shaped tube.

Although the device is shown and illustrated in conjunction with an agitator 16, the device is usable with any fermentation vessel independent of what type of agitating means is employed. Thus, tubulations 38 can be omitted.

It is noted that the gas input path, including support shaft 48, can also be used for example to deliver nutrient or other fluid. Additionally, for continuous operation, a second screened tube 76, as illustrated in FIG. 1, can be provided for drawing spent nutrient out of vessel 10, fresh nutrient being delivered through gas supply tube 68. This method is referred to as perfusion.

In a further embodiment, the agitator is driven by a shaft from below, and liquid or gas can enter from below through the motor shaft and be carried up to the top of the annular cylindrical member coupled to the top of the downwardly extending tube of the original device.

Figure 8:
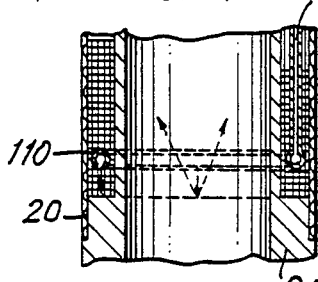
FIG. 8 is a cross-sectional view of a portion of an embodiment of the sparger in accordance with the invention including a ring-shaped tube which has apertures for release of gas into the sparger's chamber in accordance with the invention.

In an alternate embodiment shown in FIG. 8, annular channel 24 is replaced by an annular tube 110 coupled to tube 22 and formed with apertures distributed about the upper surface of tube 110.

In still another embodiment, a cylindrical screen may be mounted about the tubulations, thereby eliminating any foaming in the liquid being forced out through the tubes.

Figure 9:
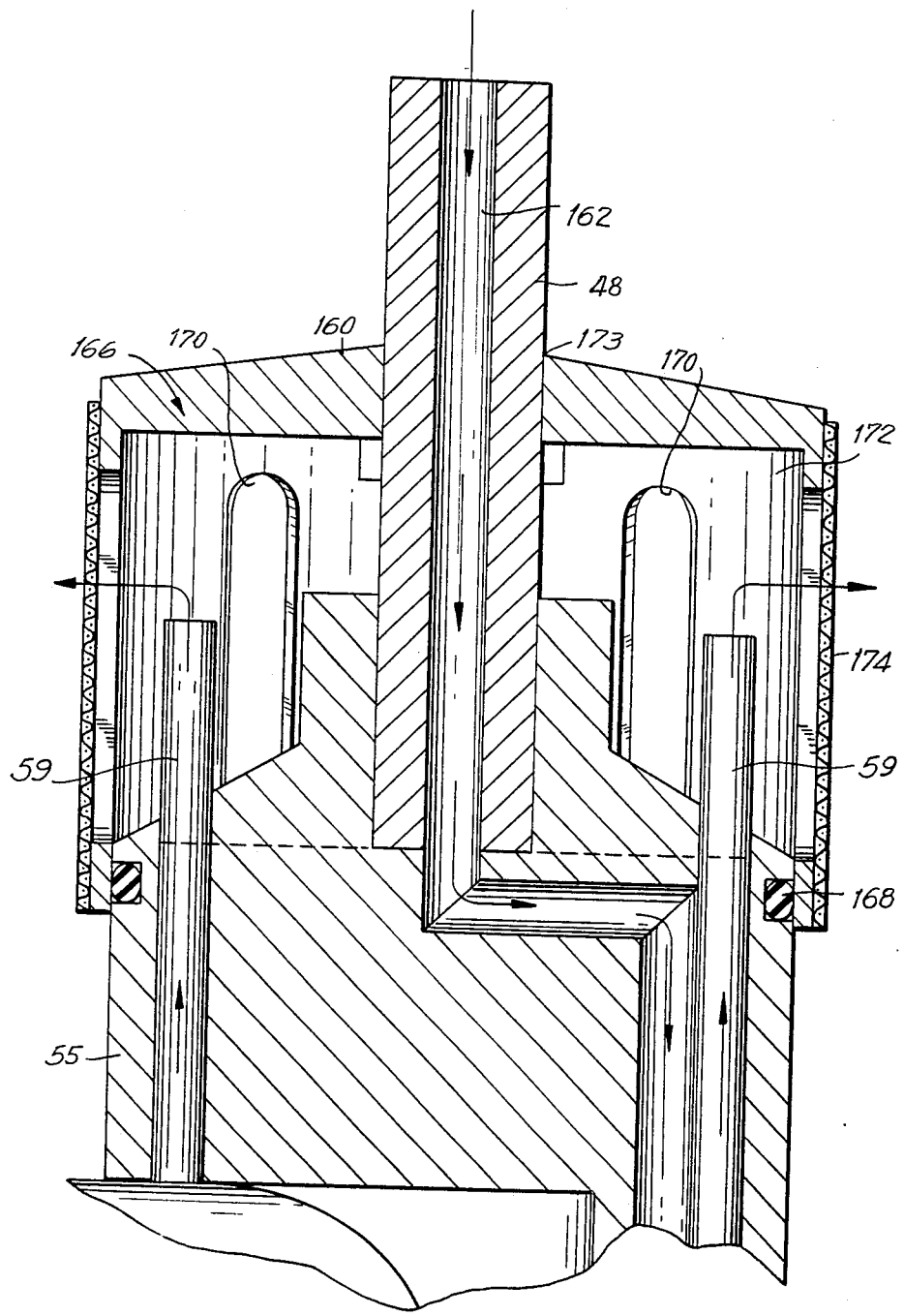
FIG. 9 is a cross-sectional view of a portion of an embodiment of the sparger in accordance with the invention including a cap member having a plurality of windows and a screen member wrapped around the cap member and covering the windows.

In yet a further embodiment, as FIG. 9 illustrates, a cylindrical screen may be mounted about tubes 59 in order to eliminate foaming in liquid being forced out tubes 59. In particular, end member 55 of the agitator supports a cap 166 and together define a chamber 172 therebetween. Cap member 166 is formed with an end wall 160 having an opening 173 in order that shaft 48 may extend through end wall 160. Cap 166 is secured to end member 55 by O-ring 168 and has a plurality of windows 170. A cylindrical screen 174 is wrapped around cap 166 in order to cover windows 170. When liquid is being forced out tubes 59, the liquid passes through screened windows 170 and then falls into the liquid in the vessel.

Figure 10:
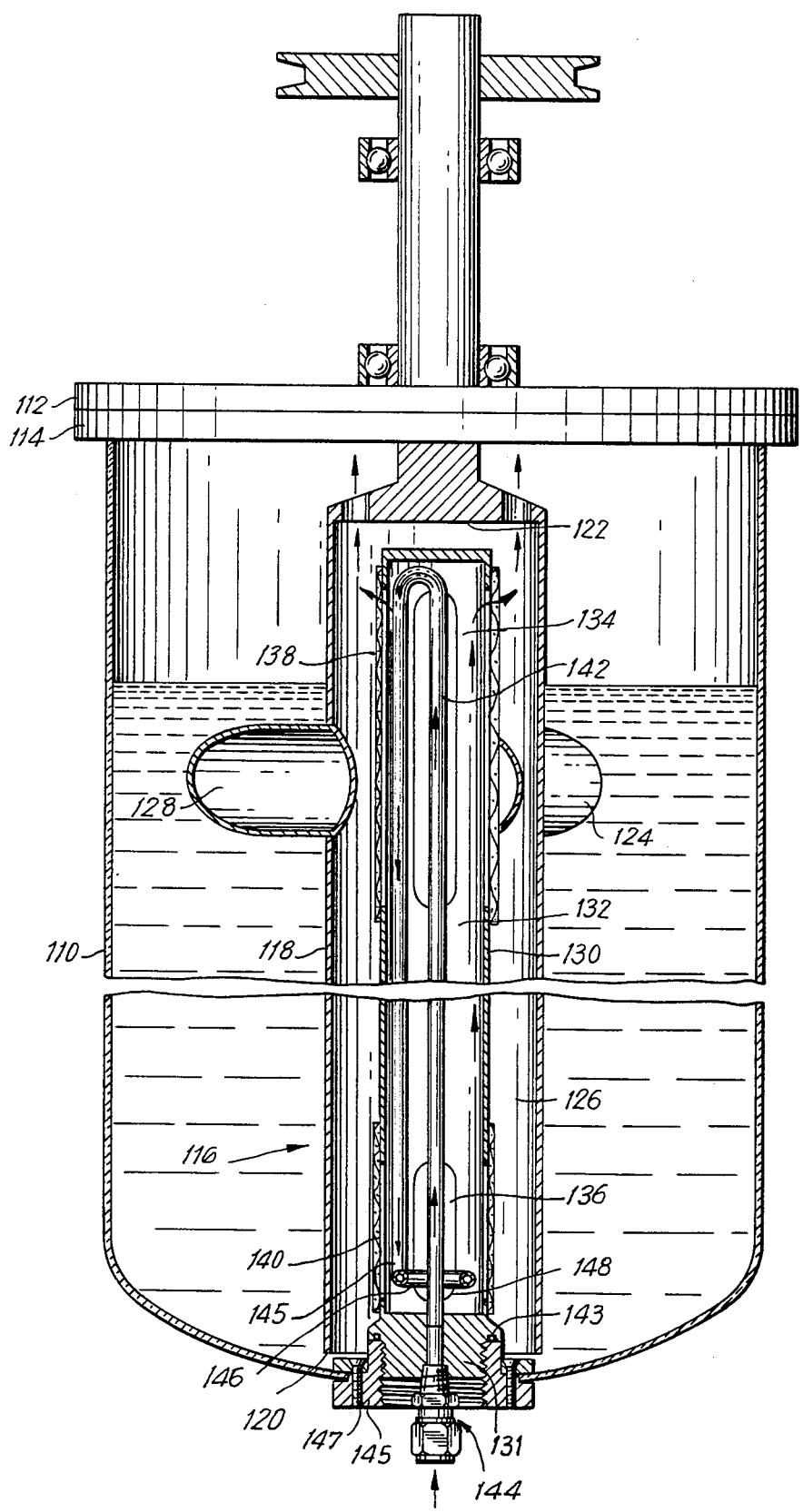
FIG. 10 is a fragmentary, cross-sectional view of an agitator using a sparger made in accordance with another embodiment of the invention.

Reference is now made to FIG. 10, which illustrate a fermentation vessel 110, containing a cylindrical agitator 116 of an alternate embodiment to that shown in FIGS. 1–9. Vessel 110 is closed by means of a vessel cap 112 which is sealed against top rim 114 of vessel 110. Agitator 116 is supported on a vessel cap 112 and includes a first open end 120 and a second closed end 122. Agitator 116 also includes an outer cylinder 118 and an inner cylinder 130, which form an annular cavity 126 therebetween.

Three tubulations 124 project laterally from outer cylinder 118 of agitation 116. Tubulations 124 are hollow and include tubulation openings 128. Tubulations 124 are constructed similarly to the tubulations of the first embodiment. As a result, a suction effect is created within agitator 116 and tubulations 124 in order to cause fluid within vessel 110 to flow into open end 120, through annular cavity 126, into tubulations 124 and out openings 128.

As shown in FIG. 10, inner cylinder 130 of agitator 116 is supported on support member 131 and defines an inner chamber 132. Inner cylinder 130 includes a plurality of upper windows 134 and lower windows 136 in order that annular cavity 126 communicates with inner chamber 132. Inner cylinder 130 further includes a first upper outer cylindrical screen 138 which overlaps upper windows 134 and a second lower outer cylindrical screen 140 which overlaps lower windows 136. A tube 142 extends longitudinally within inner chamber 132 of inner cylinder 130 and is connected at a first end 143 to a gas input 144 and at a second end 145 to an annular gas channel 146. Tube 142 is supported on support member 113 which in turn is mounted in a mounting fitting and coupled thereto by a waterproof O ring 143, screws 145 and annular seal plate 147.

In operation, air or another gas is forced under pressure through gas input 144 into tube 142 and in turn into annular gas channel 146. Since annular gas channel 146 has a plurality of aperatures 148 along its lower surface of releasing gas into inner chamber 132, gas which is released bubbles through the fluid within inner chamber 132. Due to gas pressure, the bubbling gas passes through upper and lower screens 138 and 140 which cover windows 134 and 136 respectively, but in such fine bubbles so as not to cause foaming. As a result, fluid flowing through annular cavity 126 is continuously aerated without foaming. Furthermore, excess gas is emitted by means of annular gas exit 150 in second closed end 122.

In response to measurements of dissolved oxygen and pH, the operator can determine the precise needs of the system for oxygen or other gases or liquids, which can be fed efficiently and distributed by the device. Additionally, the agitator may rotate at varying speeds depending on the needs of the system. In particular, the preferred rotation speed is between about 20 to 225 rpm. The preferred flow rate is between about 0.2 to 1.5 liters/min and the preferred working volume (maximum practical volume for the system is about 3.8 liters).

In testing, the sparger of the invention has been shown to be 10 times more effective than conventional surface aeration and just one-half as efficient as direct air sparging, but direct air sparging causes excess foam.

It will thus be seen that the objects set forth above, among those apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A sparger for cell culture reactor systems containing a liquid comprising a vertically extending chamber positioned in a liquid, said chamber defined by at least a first wall formed at least in part by a screen, and means for directing a gas into the bottom of the chamber in order to aerate said liquid, said aerated liquid passing through said screen and exit opening means proximate the top of the chamber for communication with a position above the liquid level in the cell culture reactor system.

2. The sparger of claim 1, wherein said first wall is formed by said screen and said chamber is narrow and vertically extending and said chamber is defined by a second solid inner wall and said screened wall.

3. The sparger of claim 2, wherein said second solid wall and said screened wall are essentially cylindrical to define a cylindrical chamber.

4. The sparger of claim 3, wherein said gas directing means includes an annular gas passageway having at least one entrance opening and a plurality of exit openings distributed about the length of the passageway, the passageway being positioned in a lower region of the cylindrical chamber.

5. The sparger of claim 4, wherein said gas directing means further includes at least one tube means extending in said chamber between an upper and lower wall thereof and communicating with the entrance opening of the annular gas passageway.

6. The sparger of claim 5, and including upper and lower support means for the screen for supporting the screen in spaced relation to the solid wall, said upper support means defining the top surface of said chamber and having openings therein respectively forming a part of the exit opening means and gas directing means, at least one opening forming a part of the gas directing means being coupled to said at least one tube means.

7. The sparger of claim 6, said gas directing means including means adapted to couple said at least one opening to a source of gas outside of said cell culture reactor system.

8. The sparger of claim 7, wherein said solid wall, screen and support means rotate about an essentially vertical axis.

9. The sparger of claim 8, wherein said system includes a vessel, a hollow drive shaft supporting said rotating chamber, said hollow drive shaft forming a part of said gas directing means.

10. The sparger of claim 9, wherein said solid wall is the inner wall.

11. The sparger of claim 10, wherein said solid wall extends above said screen and is formed with at least one opening therethrough in said extended region, a top wall closing the cylindrical solid wall at a point above said at least one opening, and further comprising at least one tubulation extending from said at least one opening and formed with an outer opening positioned so that when the cylindrical chamber is rotated, a suction force is created at the outer opening.

12. The sparger of claim 11, further including a screen mounted about said at least one tubulation.

13. The sparger of claim 2, wherein said solid wall is the inner wall.

14. The sparger of claim 2, further including a screen mounted about said exit opening means.

15. The sparger of claim 14, wherein said screen is mounted about said exit opening means by means of a cap member covering said exit opening means, said cap member having at least one window, said screen covering said at least one window.

16. The sparger of claim 1, wherein said chamber defined by said first wall has at least one window, said at least one window being formed by said screen, said gas directing means being adapted to direct said gas to the bottom region of said chamber, and further including exit opening means adapted to communicate to a position above the liquid level in the system.

17. The sparger of claim 16, wherein said first wall has at least one upper window along the upper portion of said wall and at least one lower window along the lower portion of said wall, said windows communicating to a position below the liquid level in the system.

18. The sparger of claim 17, wherein said wall is essentially cylindrical to define a cylindrical chamber.

19. The sparger of claim 18, wherein said gas directing means includes an annular gas passageway having at least one entrance opening and a plurality of exit openings distributed about the length of the passageway, the passageway being positioned in a lower region of the chamber.

20. The sparger of claim 19, wherein said gas directing means further includes at least one tube means extending in said chamber and communicating with the entrance opening of said annular gas passageway.

21. The sparger of claim 20, wherein said wall is supported on a lower support means, said lower support means having at least one opening for forming a part of the gas directing means being coupled to said at least one tube means.

22. The sparger of claim 21, wherein said gas directing means includes means adapted to couple said at least one opening to a source of gas outside of said cell culture reactor system.

23. The sparger of claim 22, wherein said first wall and said lower support means rotate about an essentially vertical axis.

24. The sparger of claim 23, further including a second outer solid wall surrounding said first wall and formed with at least one opening therethrough, said walls defining an outer vertically extending chamber, a top wall closing the outer solid wall at a point above said at least one opening, and further including at least one tubulation extending from at least one opening and formed within an outer opening positioned so that when the vertically extending chamber is rotated, a suction force is created at said outer opening.

25. The sparger of claim 24, wherein said system includes a vessel and a hollow drive shaft supporting said rotating chambers.

* * * * *